United States Patent
Ninomiya et al.

(10) Patent No.: US 10,085,636 B2
(45) Date of Patent: Oct. 2, 2018

(54) EYE GAZE DETECTION APPARATUS AND EYE GAZE DETECTION METHOD

(71) Applicant: JVC KENWOOD Corporation, Yokohama-shi (JP)

(72) Inventors: Masaru Ninomiya, Yokohama (JP); Katsuyuki Shudo, Yokohama (JP); Shuji Hakoshima, Yokohama (JP)

(73) Assignee: JVC KENWOOD Corporation, Yokohama-shi (JP)

( * ) Notice: Subject to any disclaimer, the term of this patent is extended or adjusted under 35 U.S.C. 154(b) by 66 days.

(21) Appl. No.: 14/918,262

(22) Filed: Oct. 20, 2015

(65) Prior Publication Data
US 2016/0113486 A1    Apr. 28, 2016

(30) Foreign Application Priority Data

Oct. 24, 2014 (JP) ................. 2014-217651

(51) Int. Cl.
*A61B 3/14* (2006.01)
*A61B 3/113* (2006.01)
(Continued)

(52) U.S. Cl.
CPC ............ *A61B 3/113* (2013.01); *A61B 3/0025* (2013.01); *A61B 3/107* (2013.01); *A61B 3/14* (2013.01);
(Continued)

(58) Field of Classification Search
CPC .. A61B 3/10; A61B 3/11; A61B 3/107; A61B 3/113; A61B 3/0025; A61B 3/14;
(Continued)

(56) References Cited

U.S. PATENT DOCUMENTS

2003/0123027 A1*  7/2003  Amir ................. G06K 9/00604
                                                                351/209
2010/0328444 A1* 12/2010  Blixt ..................... A61B 3/113
                                                                348/78

FOREIGN PATENT DOCUMENTS

EP      2976990 A1   1/2016
JP      2739331 B2   1/1998
(Continued)

OTHER PUBLICATIONS

Extended Search Report in European Patent Application No. 15190678.1, dated Feb. 26, 2016.

*Primary Examiner* — Mustak Choudhury
(74) *Attorney, Agent, or Firm* — Venable LLP; Michael A. Sartori; Laura G. Remus

(57) ABSTRACT

An eye gaze detection apparatus includes a plurality of illuminators each including a light source for emitting light and disposed symmetrically with respect to a predetermined position, a plurality of imaging units each disposed at an inner or outer position with respect to the plurality of illuminators, a position detector configured to detect a first position indicating a pupil center and a second position indicating a corneal reflection center based on an image of an eyeball of a subject, the image being captured by the imaging unit with the light emitted by the illuminator, and a calculator configured to calculate a fourth position indicating a corneal curvature center, based on the predetermined position, a third position on a display, the first position, and the second position.

3 Claims, 13 Drawing Sheets

(51) Int. Cl.
  *A61B 3/107*    (2006.01)
  *A61B 3/00*     (2006.01)
  *G06K 9/00*     (2006.01)
  *G06K 9/20*     (2006.01)
  *A61B 3/11*     (2006.01)

(52) U.S. Cl.
  CPC ....... *G06K 9/00604* (2013.01); *G06K 9/2027* (2013.01); *A61B 3/11* (2013.01)

(58) Field of Classification Search
  CPC .. A61B 3/145; A61B 3/0008; G06K 9/00604; G06K 9/2027; G06K 9/60; G06K 9/0061; G06F 3/01; G06F 3/013; G06F 3/04842; G06F 21/84; G06T 7/73
  USPC ........ 351/200, 209, 210, 211, 246; 345/156, 345/419, 633; 348/78; 396/51
  See application file for complete search history.

(56) References Cited

FOREIGN PATENT DOCUMENTS

| | | |
|---|---|---|
| JP | 4824420 B2 | 9/2011 |
| WO | WO-2014/136803 A1 | 9/2014 |
| WO | WO-2015/08003 A1 | 6/2015 |

\* cited by examiner

EYE GAZE DETECTION APPARATUS AND EYE GAZE DETECTION METHOD

CROSS-REFERENCE TO RELATED APPLICATION(S)

The present application claims priority to and incorporates by reference the entire contents of Japanese Patent Application No. 2014-217651 filed in Japan on Oct. 24, 2014.

BACKGROUND OF THE INVENTION

1. Field of the Invention

The present invention relates to an eye gaze detection apparatus and an eye gaze detection method.

2. Description of the Related Art

An eye gaze detection apparatus has been proposed for detecting a gaze position of an operator or a subject on a viewing surface such as a monitor screen. For example, a method to achieve a non-contact eye gaze detection that reliably detects an eye gaze direction without attaching any device to a face of the subject has been known. With this method, an on-eyeball reflection of light emitted from a light source is detected to calculate a pupil center and a corneal curvature center, and then a line that connects the pupil center and the corneal curvature center is detected as an eye gaze.

According to a method stated in Japanese Patent No. 2739331, two cameras and two light sources are used to detect two corneal reflection points within an eyeball. The corneal curvature center is calculated from these two corneal reflection points, and the eye gaze is detected based on a positional relationship between this corneal curvature center and a pupil center. According to a method stated in Japanese Patent No. 4824420, by using one camera and two light sources, the corneal curvature center is calculated from a line of intersection of planes, each plane containing two corneal reflection points. The eye gaze is detected based on the positional relationship between the corneal curvature center and the pupil center.

The methods stated in the above-described documents, however, have had a problem that the apparatus to detect an eye gaze with high accuracy becomes complicated in configuration and large in size. For example, when using two light sources, two reflection points corresponding to the respective light sources are detected separately, and thus, the two light sources need to have a predetermined minimum distance therebetween. This is because if the distance between the two light sources is too short, the two reflection points might overlap, making it difficult to separate them from each other.

Therefore, there is a need for an eye gaze detection apparatus and an eye gaze detection method to be capable of achieving improved detection accuracy.

SUMMARY OF THE INVENTION

It is an object of the present invention to at least partially solve the problems in the conventional technology.

There is provided an eye gaze detection apparatus that includes a plurality of illuminators each including a light source for emitting light and disposed symmetrically with respect to a predetermined position, a plurality of imaging units each disposed at an inner or outer position with respect to the plurality of illuminators, a position detector configured to detect a first position indicating a pupil center and a second position indicating a corneal reflection center based on an image of an eyeball of a subject, the image being captured by the imaging unit with the light emitted by the illuminator, and a calculator configured to calculate a fourth position indicating a corneal curvature center, based on the predetermined position, a third position on a display, the first position, and the second position.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
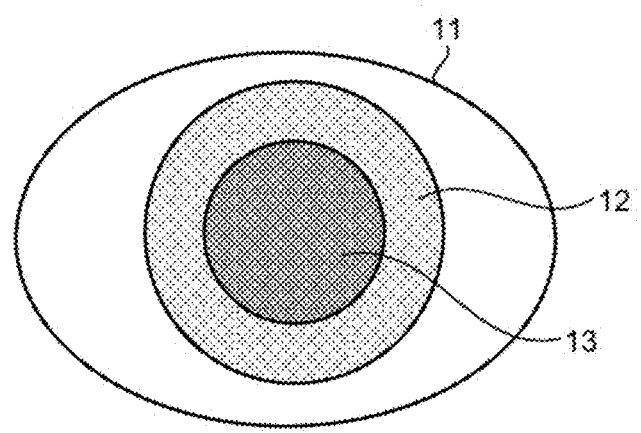
FIG. 1 is a diagram illustrating an appearance of an eye of a subject when one light source is used.

An eye gaze detection apparatus and an eye gaze detection method according to embodiments of the present invention will be described in detail with reference to the drawings. Note that the present invention is not limited by these embodiments. Hereafter, an exemplary application of an eye gaze detection apparatus as a diagnosis support apparatus to assist diagnosing a developmental disorder or the like based on a result of an eye gaze detection will be described. An applicable apparatus is not limited to the diagnosis support apparatus.

The eye gaze detection apparatus (diagnosis support apparatus) of the present embodiment detects an eye gaze by using illuminators disposed at two positions. The eye gaze detection apparatus (diagnosis support apparatus) of the present embodiment calculates a corneal curvature center position with high accuracy based on a result of a measurement performed before the eye gaze detection while having a subject gaze at a point.

Note that the illuminator is a component that includes a light source and can illuminate an eyeball of the subject with light. The light source is a light emitting device, for example, a light emitting diode (LED). The light source may be formed of one LED or a plurality of LEDs in combination to be disposed at one position. Hereafter, a "light source" may be used as above as a term to indicate the illuminator.

Achieving an accurate detection of a gaze point requires an accurate detection of a pupil position. It is known that, if imaging is performed using a camera with a near-infrared light source lit and with a distance between the camera and the light source longer than a predetermined value, a pupil becomes darker than other portions. The pupil position is detected by using this feature.

To simplify the apparatus, it is possible to use a configuration using one light source instead of two. For example, one light source may be disposed at a center between the two cameras, where an image is captured by the two cameras with the light source lit. In such a configuration, an insufficient distance between the camera and the light source has caused, depending on the subject, a difficulty in darkening the pupil enough to be distinguished from an iris.

Another possible method to darken the pupil would be using a near-infrared light source having a different wavelength and higher light-absorbance. Camera sensitivity for this wavelength, however, has been known to be low and to degrade image processing accuracy.

Accordingly, in the present embodiment, the light sources are disposed at two positions, at outer positions of the two corresponding cameras. While these two light sources are lit at mutually different timings, imaging is performed with the camera that is more distant (disposed farther) from the lit light source. This achieves capturing a darker image of the pupil and distinguishing the pupil from the other portions with higher accuracy.

In this case, since different light sources are used for illumination, it is difficult to simply apply an ordinary three-dimensional measurement using a stereo method. That is, it is difficult to calculate a line connecting the light source and a corneal reflection to be used in acquiring the gaze point in world coordinates. Therefore, in the present embodiment, a mutual positional relationship between the cameras for imaging, and a mutual positional relationship between the light sources to light, at two timings, are determined to be symmetrical with respect to a position of a virtual light source (virtual light source position). Two coordinate values obtained when the two individual light sources are lit are respectively determined as a coordinate value obtained by a left camera and a coordinate value obtained by a right camera, and the values are converted into the world coordinates. Consequently, by using a corneal reflection position obtained when each of the two light sources is lit, the line connecting the virtual light source and the corneal reflection is able to be calculated in the world coordinates, and the gaze point is able to be calculated on the basis of this line.

Figure 2:
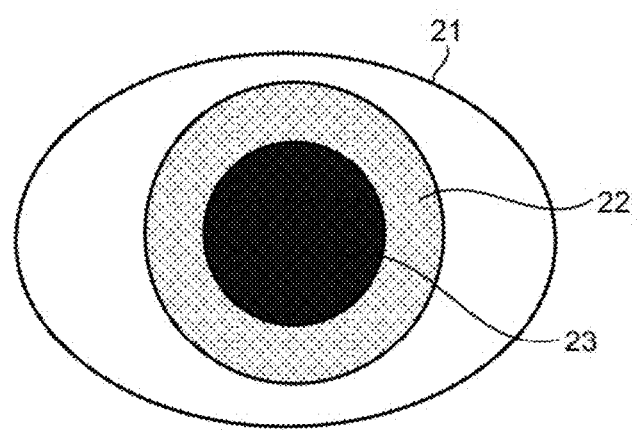
FIG. 2 is a diagram illustrating an appearance of an eye of the subject when two light sources are used.

FIG. 1 is a diagram illustrating an appearance of an eye 11 of a subject when one light source is used. As illustrated in FIG. 1, a difference of darkness between an iris 12 and a pupil 13 is insufficient, making it difficult for them to be distinguished from each other. FIG. 2 is a diagram illustrating an appearance of an eye 21 of a subject when two light sources are used. As illustrated in FIG. 2, the difference of darkness between an iris 22 and a pupil 23 is higher than that in FIG. 1.

Figure 3:
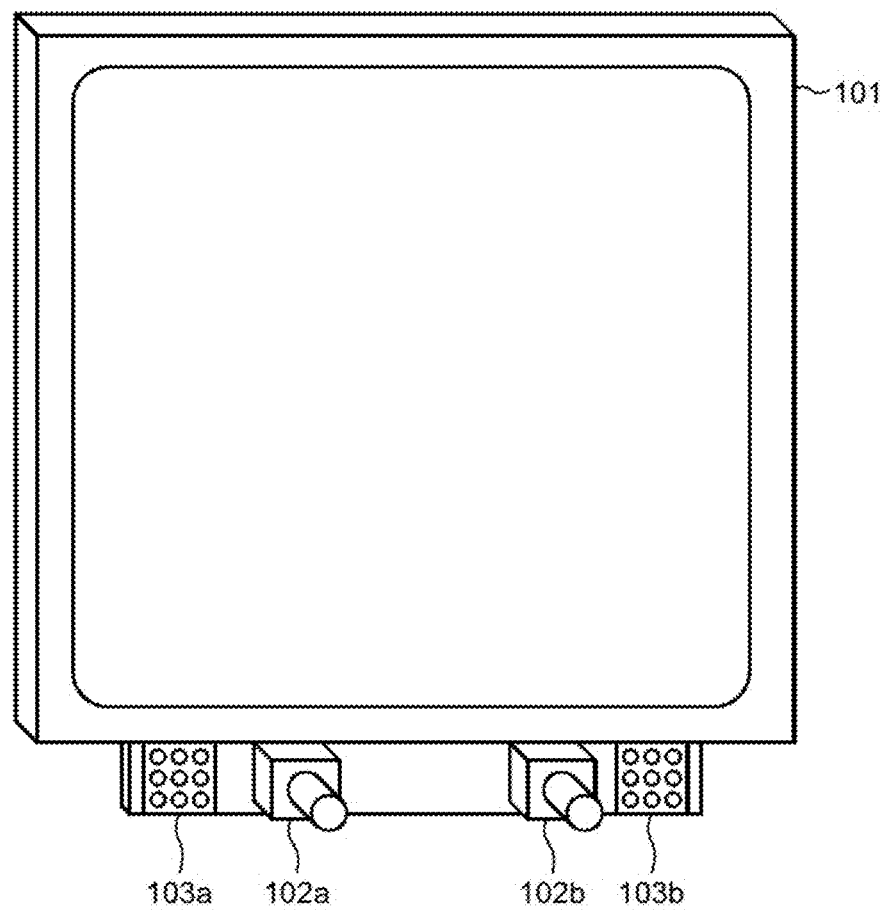
FIG. 3 is a diagram illustrating an exemplary arrangement of a display, a stereo camera, an infrared light source of the present embodiment.
Figure 4:
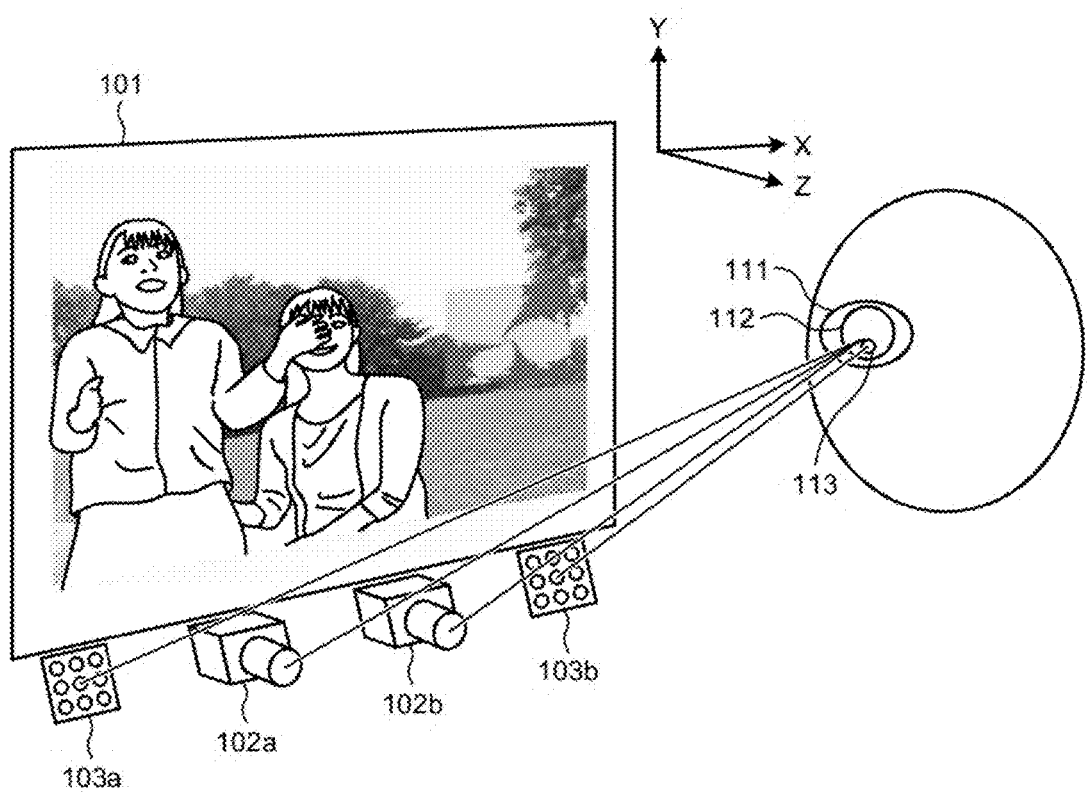
FIG. 4 is a diagram illustrating an exemplary arrangement of a display, a stereo camera, an infrared light source, and a subject of the present embodiment.

FIGS. 3 and 4 are diagrams illustrating an exemplary arrangement of a display, a stereo camera, an infrared light source, and the subject of the present embodiment.

As illustrated in FIG. 3, the diagnosis support apparatus of the present embodiment includes a display 101, right and left cameras 102a and 102b to form a stereo camera, and LED light sources 103a and 103b. The right and left cameras 102a and 102b are disposed beneath the display 101. The LED light sources 103a and 103b are disposed at the outer positions of the right and left cameras 102a and 102b, respectively. The LED light sources 103a and 103b are light sources for emitting, for example, near-infrared light with a wavelength of 850 nm. FIG. 3 illustrates an exemplary configuration of the LED light sources 103a and 103b (illuminators), each formed of nine LEDs. Each of the right and left cameras 102a and 102b includes a lens that can transmit near-infrared light with a wavelength of 850 nm. Positions of the LED light sources 103a and 103b, and the positions of the right and left cameras 102a and 102b are interchangeable. The LED light sources 103a and 103b may be disposed at the inner positions of the right and left cameras 102a and 102b, respectively.

As illustrated in FIG. 4, the LED light sources 103a and 103b illuminate an eyeball 111 of the subject with near-infrared light. The left camera 102b performs imaging during illumination with the LED light source 103a. The right camera 102a performs imaging during the illumination with the LED light source 103b. Appropriately setting the positional relationship between the right and left cameras 102a and 102b and the LED light sources 103a and 103b darkens a pupil 112 by low-luminance reflection and brightens corneal reflection 113 generated inside the eyeball 111 as a virtual image with high-luminance reflection in an image to be captured. Accordingly, on-image positions of the pupil 112 and the corneal reflection 113 can be obtained by the two cameras, i.e., the right and left cameras 102a and 102b, respectively.

Based on the positions of the pupil 112 and the corneal reflection 113 obtained by the two cameras, three-dimensional world coordinate values for the positions of the pupil 112 and the corneal reflection 113 are calculated. The present embodiment defines three-dimensional world coordinates such that a Y-coordinate represents a height (upper direction is indicated by +), an X-coordinate represents a width (right-hand direction is indicated by +), and a Z-coordinate represents a depth (front direction is indicated by +), with respect to a center position of the screen of the display 101 as an origin.

Figure 5:
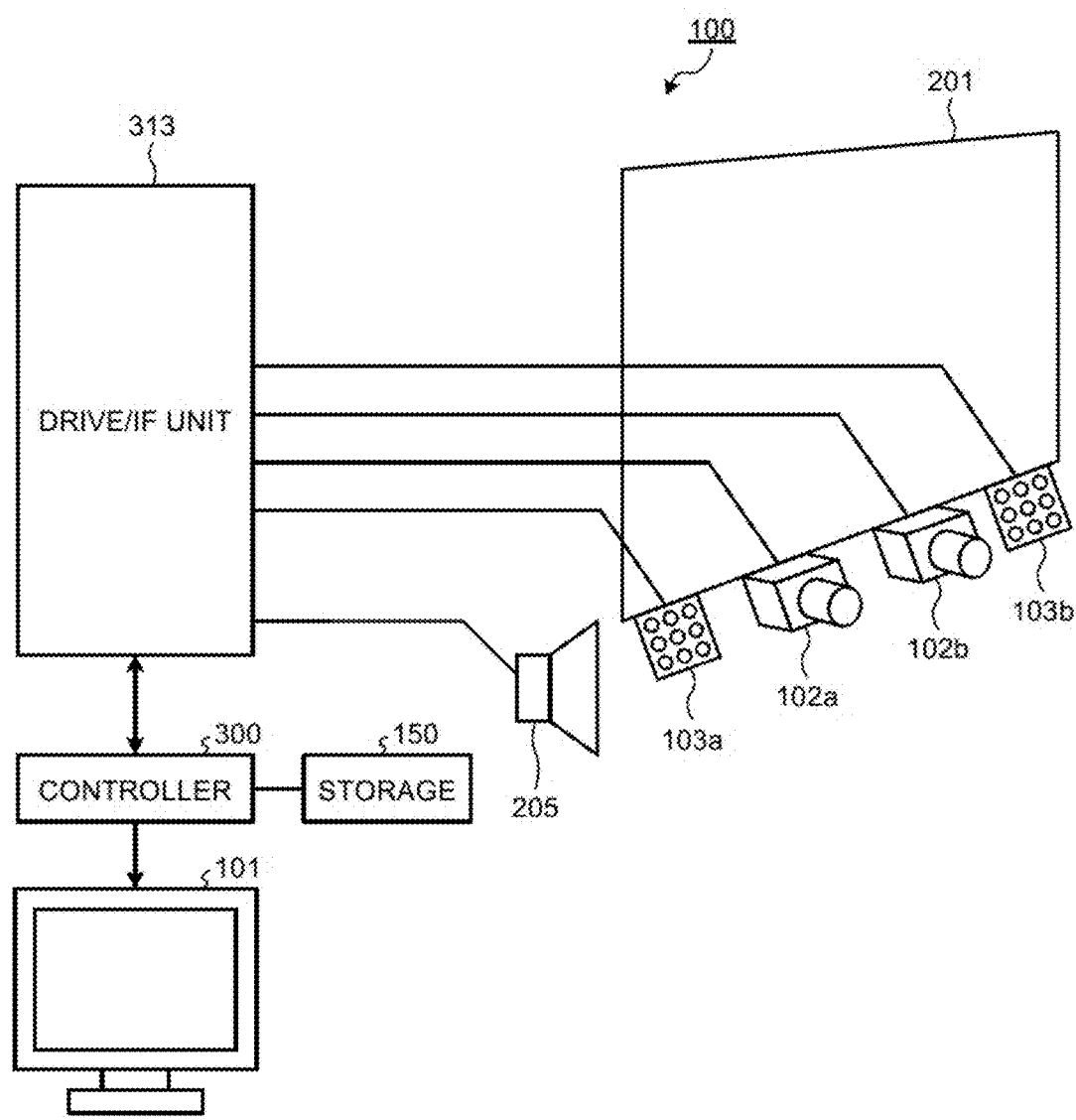
FIG. 5 is a schematic diagram illustrating a function of a diagnosis support apparatus.

FIG. 5 is a schematic functional diagram of a diagnosis support apparatus 100. FIG. 5 illustrates a part of the configurations illustrated in FIGS. 3 and 4, and a configuration to be used for driving the configurations or the like. As illustrated in FIG. 5, the diagnosis support apparatus 100 includes the right and left cameras 102a and 102b, the LED light source 103a for the left camera 102b, the LED light source 103b for the right camera 102a, a speaker 205, a drive/interface (IF) 313, a controller 300, a storage 150, and the display 101. In FIG. 5, a display screen 201 clearly indicates the positional relationship between the right and left cameras 102a and 102b. The display screen 201 is a screen displayed on the display 101. The driver and the IF may be disposed in combination or separately.

The speaker 205 functions as an audio output unit that outputs voice, etc. for alerting the subject at calibration or the like.

The drive/IF 313 drives each component included in the stereo camera. The drive/IF 313 also functions as an interface between each component included in the stereo camera and the controller 300.

The controller 300 can be implemented, for example, by a computer including a control device such as a central processing unit (CPU), a storage device such as a read only memory (ROM) and a random access memory (RAM), a communication I/F to perform communication via a connected network, and a bus to connect individual units.

The storage 150 stores various types of information such as a control program, a measurement result, and a diagnosis support result. The storage 150 stores, for example, an image to be displayed on the display 101. The display 101 displays various types of information such as a target image for diagnosis.

Figure 6:
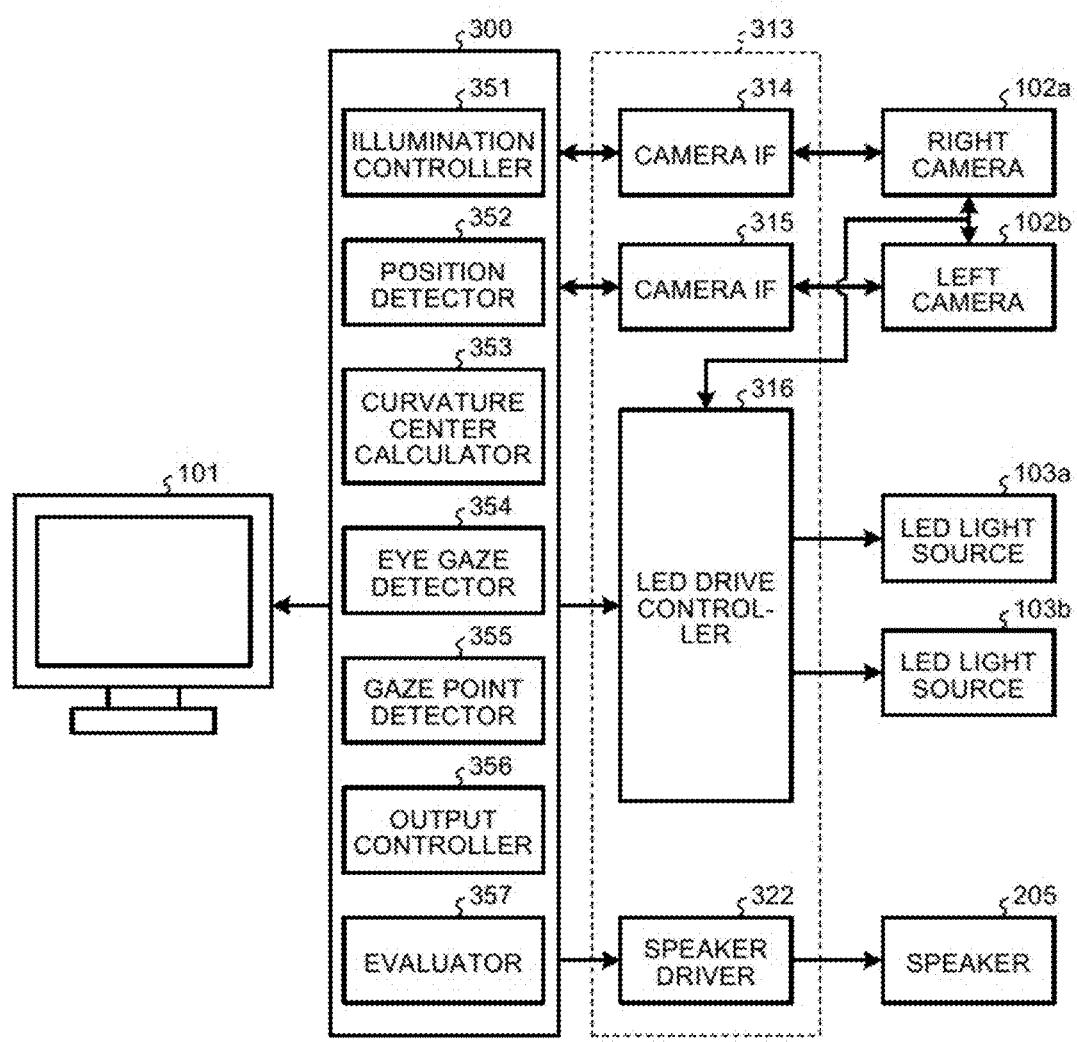
FIG. 6 is a block diagram illustrating an exemplary detailed function of each component illustrated in FIG. 5.

FIG. 6 is a block diagram illustrating an exemplary detailed function of each component illustrated in FIG. 5. As illustrated in FIG. 6, the display 101 and the drive/IF 313 are connected to the controller 300. The drive/IF 313 includes camera IFs 314 and 315, an LED drive controller 316, and a speaker driver 322.

The right and left cameras 102a and 102b are connected to the drive/IF 313 via the camera IFs 314 and 315, respectively. The drive/IF 313 drives these cameras to image the subject. The right camera 102a outputs a frame synchronization signal. The frame synchronization signal is input to the left camera 102b and the LED drive controller 316. As a result, the LED light sources 103a and 103b are lit and the images obtained by the right and left cameras are captured correspondingly.

The speaker driver 322 drives the speaker 205. The diagnosis support apparatus 100 may include an interface (printer IF) for connecting with a printer as a printing unit. The printer may be provided inside the diagnosis support apparatus 100.

The controller 300 controls the overall diagnosis support apparatus 100. The controller 300 includes an illumination controller 351, a position detector 352, a curvature center calculator 353, an eye gaze detector 354, a gaze point detector 355, an output controller 356, and an evaluator 357. Note that the eye gaze detection apparatus may include at least the illumination controller 351, the position detector 352, the curvature center calculator 353, and the eye gaze detector 354.

Each component included in the controller 300, namely, the illumination controller 351, the position detector 352, the curvature center calculator 353, the eye gaze detector 354, the gaze point detector 355, the output controller 356, and the evaluator 357, may be implemented as software (program) and/or a hardware circuit.

In the case of implementation as a program, the program is provided as a computer program product as a file in an installable form or an executable form, stored on a computer-readable recording medium such as a compact disk read only memory (CD-ROM), a flexible disk (FD), a compact disk recordable (CD-R), and a digital versatile disk (DVD). The program may be stored on a computer connected to a network such as the Internet and may be downloaded and provided via the network. Alternatively, the program may be provided or distributed via the network such as the Internet. Also, the program may be stored in a ROM, etc. in advance and provided.

The illumination controller 351 uses the LED drive controller 316 to control lighting of the LED light sources 103a and 103b. For example, the illumination controller 351 controls the LED light sources 103a and 103b such that they are lit at mutually different timings. The timing difference (time) may be predetermined as the time that has substantially no influence on the result of the eye gaze detection due to, for example, the moving eye gaze of the subject.

The position detector 352 calculates a pupil center position (first position) indicating a center of the pupil based on the image of the eyeball captured by the stereo camera. The position detector 352 also calculates a corneal reflection center position (second position) indicating a center of the corneal reflection based on the captured image of the eyeball.

The curvature center calculator 353 calculates a corneal curvature center (fourth position) based on a line (first line) connecting the virtual light source position and the corneal reflection center position. For example, the curvature center calculator 353 calculates, as the corneal curvature center, a position where a distance from the corneal reflection center on this line is equal to a predetermined value. The predetermined value may be a value determined beforehand based on an ordinary corneal curvature radius value or the like.

Since the corneal curvature radius value might include an individual variation, calculating the corneal curvature center based on the predetermined value might cause a large error. Therefore, the curvature center calculator 353 may calculate the corneal curvature center considering the individual variation. The curvature center calculator 353, in this case, uses the pupil center and the corneal reflection center, both of which have been calculated while having the subject gaze at a target position (third position), and calculates an intersection of a line (second line) connecting the pupil center and the target position and the line (first line) connecting the corneal reflection center and the virtual light source position. The curvature center calculator 353 calculates a distance (first distance) between the pupil center and the calculated intersection and stores the distance in the storage 150, for example.

The target position only needs to be a predetermined position by which the three-dimensional world coordinate values can be calculated. For example, a center position on the display screen 201 (origin of the three-dimensional world coordinates) may be determined as the target position. In this case, for example, the output controller 356 displays an image (target image) etc. at which the subject gazes, at the target position (center) on the display screen 201. This can allow the subject to gaze at the target position.

The target image may be any image that can catch the attention of the subject. For example, an image having a variable display manner such as luminance or color and an image having a distinctive display manner compared with other areas can be used as the target image.

Note that the target position need not be at the center of the display screen 201 but may be any position. When the center of the display screen 201 is determined as the target position, the distance to any end portion of the display screen 201 is minimized. Accordingly, a measurement error at a time of the eye gaze detection can be reduced, for example.

Processes up to the calculation of the distance are assumed to have been executed before a start of an actual eye gaze detection. In executing the eye gaze detection, the curvature center calculator 353 calculates, as the corneal curvature center, the position on the line connecting the virtual light source position and the corneal reflection center so that the distance from the pupil center is equal to the distance calculated beforehand. The curvature center calculator 353 corresponds to a calculator configured to calculate the corneal curvature center (fourth position) based on the virtual light source position, the predetermined position (third position) on the display to indicate the target image, the pupil center position, and the corneal reflection center position.

The eye gaze detector 354 detects an eye gaze of the subject based on the pupil center and the corneal curvature center. The eye gaze detector 354 detects, for example, a direction from the corneal curvature center to the pupil center as an eye gaze direction of the subject.

The gaze point detector 355 detects the gaze point of the subject using the detected eye gaze direction. The gaze point detector 355 detects, for example, the gaze point, the point at which the subject gazes on the display screen 201. The gaze point detector 355 detects, as the gaze point of the subject, an intersection of an eye gaze vector and an X-Y plane, expressed in the three-dimensional world coordinates as illustrated in FIG. 2, for example.

The output controller 356 controls output of various types of information to the display 101, the speaker 205 or the like. For example, the output controller 356 outputs the target image at the target position on the display 101. The output controller 356 also controls the output to the display 101, such as a diagnostic image and an evaluation result from the evaluator 357 or the like.

The diagnostic image may be any image corresponding to an evaluation process based on the eye gaze (gaze point) detection result. In diagnosing a developmental disorder, for example, it is appropriate to use the diagnostic images including an image favored by the subject with the developmental disorder (video of a geometric pattern, etc.) as well as another image (video of a human, etc.).

The evaluator 357 executes the evaluation process based on the diagnostic image and the gaze point detected by the gaze point detector 355. In diagnosing a developmental disorder, for example, the evaluator 357 analyzes the diagnostic image and the gaze point and evaluates whether the subject with the developmental disorder has gazed at his/her favored image.

Figure 7:
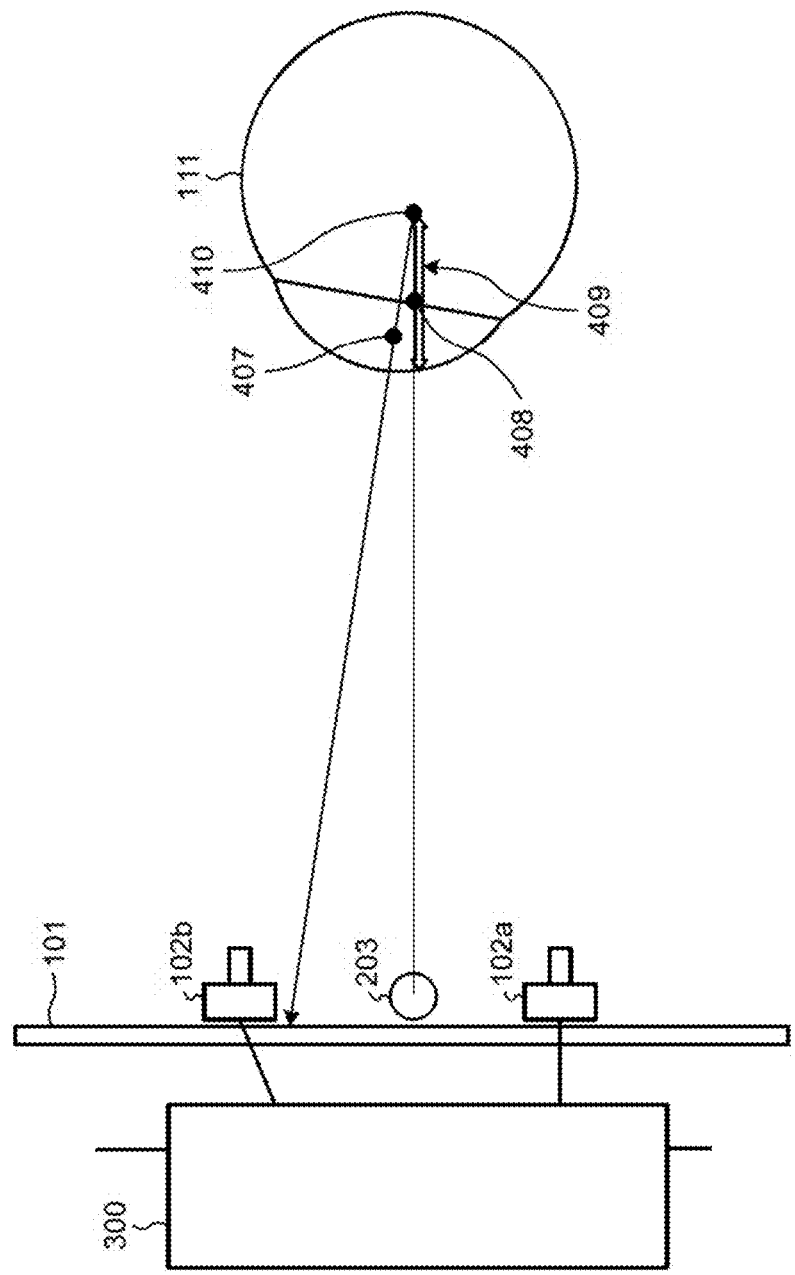
FIG. 7 is a schematic diagram illustrating a process when one light source is assumed to be used.

FIG. 7 is a schematic diagram illustrating a process where one light source is assumed to be used. The same reference signs are given to the components described in FIGS. 3 to 6 and the description thereof will be omitted. FIG. 7 is an exemplary diagram in which an LED light source 203 is used instead of the two LED light sources 103a and 103b.

A pupil center 407 and a corneal reflection center 408 represent a center of a pupil and a center of a corneal reflection point, respectively, detected when the LED light source 203 is lit. A corneal curvature radius 409 represents a distance from a corneal surface to a corneal curvature center 410. The LED light source 203 here is formed of one LED. Alternatively, the LED light source 203 may be formed of several small LEDs in combination to be disposed at one position.

Figure 8:
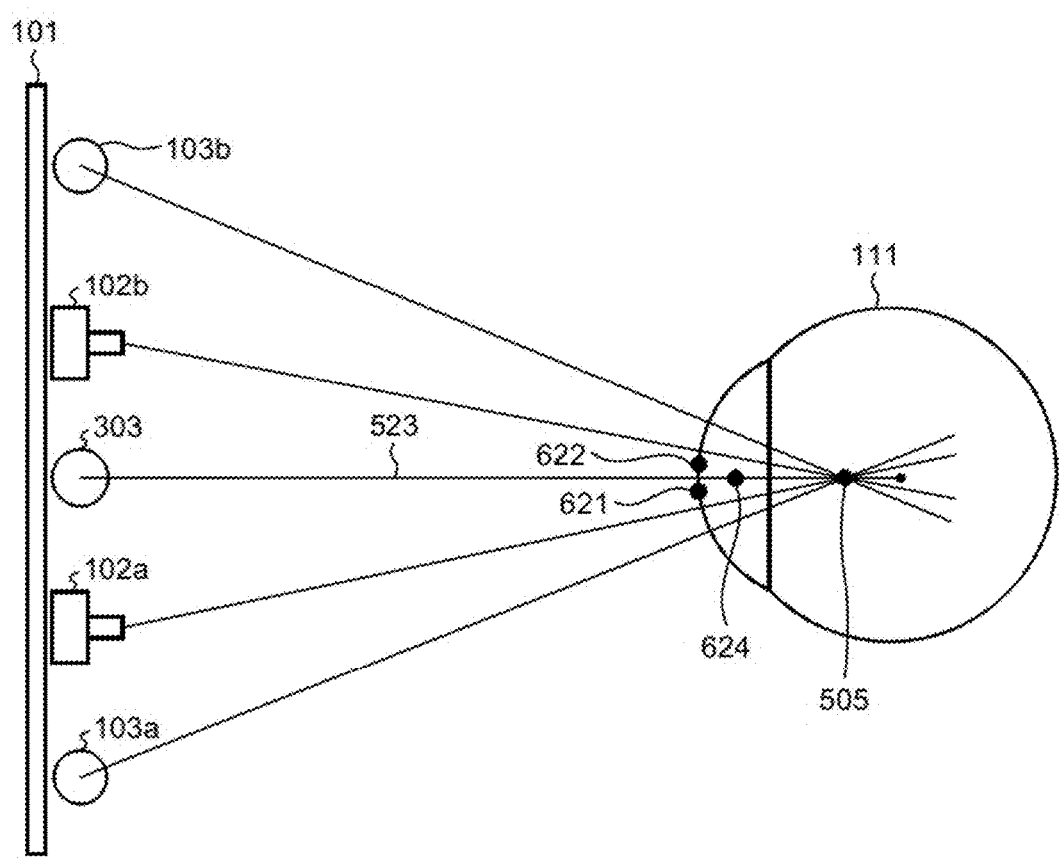
FIG. 8 is a schematic diagram illustrating a process to be executed by a diagnosis support apparatus according to the present embodiment.

FIG. 8 is a schematic diagram illustrating a process to be executed by the diagnosis support apparatus 100 of the present embodiment. The same reference signs are given to the components described in FIGS. 3 to 6 and the description thereof will be omitted.

A corneal reflection point 621 represents a corneal reflection point on the image captured with the left camera 102b. A corneal reflection point 622 represents a corneal reflection point on the image captured with the right camera 102a. In the present embodiment, the right camera 102a and the LED light source 103b for the right camera, as well as the left camera 102b and the LED light source 103a for the left camera, for example, are arranged symmetrically with respect to the line passing through the middle position between the right and left cameras 102a and 102b, for example. Therefore, a virtual light source 303 can be assumed to exist at a middle position between the right and left cameras 102a and 102b (virtual light source position). A corneal reflection point 624 represents a corneal reflection point that corresponds to the virtual light source 303. The world coordinate values for the corneal reflection point 624 can be calculated by converting the coordinate values of the corneal reflection point 621 and the corneal reflection point 622. This calculation uses a conversion parameter to convert the coordinate values obtained by the left/right cameras into the three-dimensional world coordinates. A corneal curvature center 505 exists on a line 523 connecting the virtual light source 303 and the corneal reflection point 624. Therefore, the gaze point can be detected in a similar manner to the eye gaze detection method using one light source as illustrated in FIG. 7.

The positional relationship between the right and left cameras 102a and 102b, and the positional relationship between the LED light sources 103a and 103b are not limited to the above-described positional relationships. For example, the positions may be symmetrical with respect to the same line. The right and left cameras 102a and 102b, and the LED light sources 103a and 103b need not be on the same line.

Figure 9:
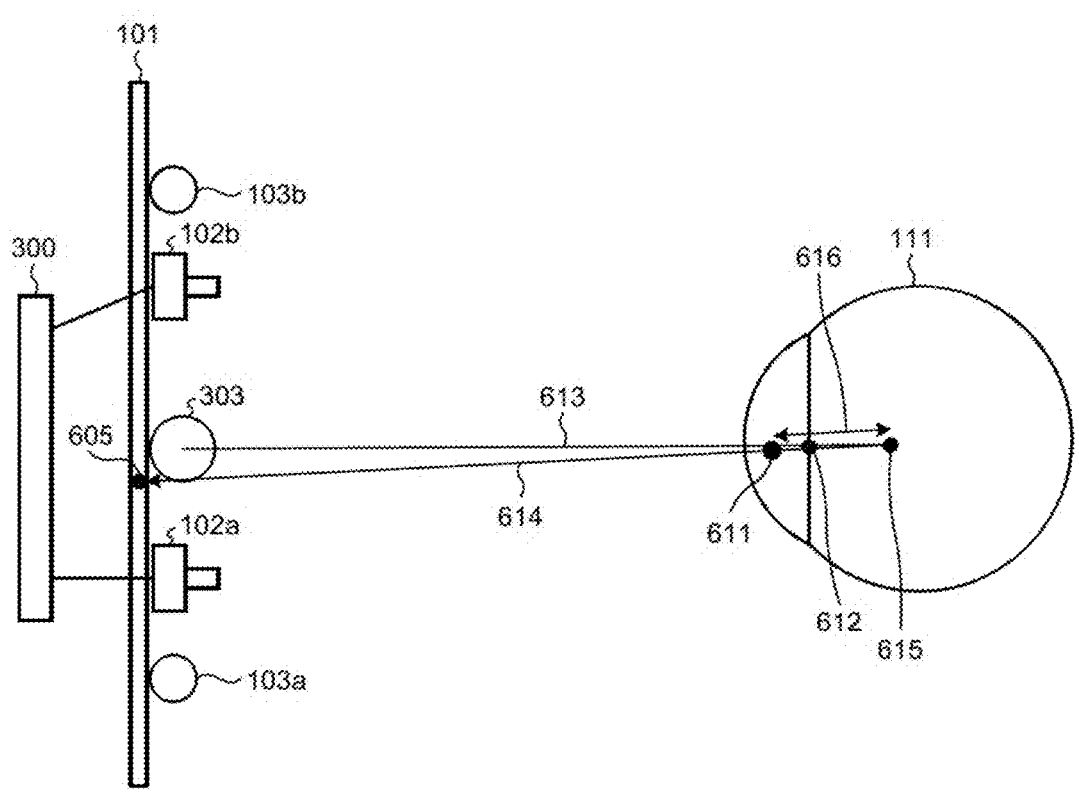
FIG. 9 is a diagram illustrating a calculation process to calculate a distance between a pupil center position and a corneal curvature center position.

FIG. 9 is a diagram illustrating a calculation process for calculating the position of the corneal curvature center, and calculating the distance between the pupil center position and the corneal curvature center position. This calculation process is executed before the gaze point detection (eye gaze detection). The same reference signs are given to the components described in FIGS. 3 to 6 and the description thereof will be omitted.

A target position 605 is a position to cause the subject to gaze at by displaying the target image, etc. at a point on the display 101. In the present embodiment, the target position 605 is assumed to be at the center position of the screen of the display 101. A line 613 is a line connecting the virtual light source 303 and a corneal reflection center 612. A line 614 is a line connecting the target position 605 (gaze point) at which the subject gazes and a pupil center 611. A corneal curvature center 615 is an intersection of the line 613 and the line 614. The curvature center calculator 353 calculates and stores a distance 616 between the pupil center 611 and the corneal curvature center 615.

Figure 10:
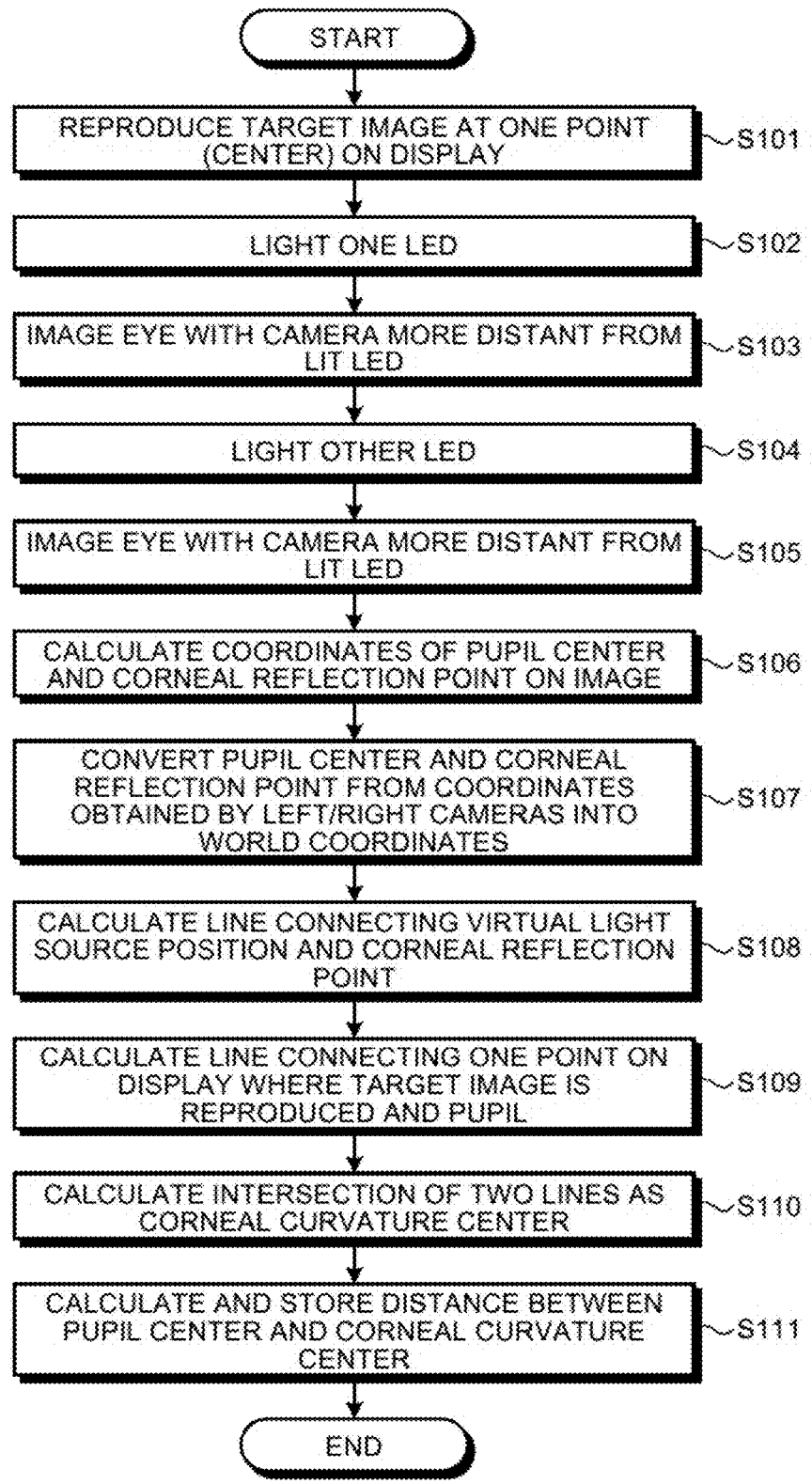
FIG. 10 is a flowchart illustrating an exemplary calculation process of the present embodiment.

FIG. 10 is a flowchart illustrating an exemplary calculation process of the present embodiment.

The output controller 356 initially reproduces the target image at a point on the screen of the display 101 (step S101), and has the subject gaze at the point. Then, the illumination controller 351 operates the LED drive controller 316 to light one of the LED light sources 103a and 103b toward the eye of the subject (step S102). The controller 300 images the eye of the subject by the right camera 102a or the left camera 102b, whichever is more distant from the lit LED light source (step S103). The illumination controller 351 then lights the other one of the LED light sources 103a and 103b toward the eye of the subject (step S104). The controller 300 images the eye of the subject by the right camera 102a or the left camera 102b, whichever is more distant from the lit LED light source (step S105).

Note that imaging by using the camera other than the camera more distant from the lit LED light source need not be stopped. That is, it may be sufficient if the camera more distant from the lit LED light source has imaged the eye of the subject and the captured image has been available in a coordinate calculation, etc.

Under the illumination from the LED light sources 103a or 103b, a pupil portion is detected as a dark portion (dark pupil). In addition, a virtual image of the corneal reflection is generated as a reflection of the LED illumination, and the corneal reflection point (corneal reflection center) is detected as a bright portion. That is, the position detector 352 detects the pupil portion from the captured image and calculates the coordinates indicating the pupil center position. For example, the position detector 352 detects, among a predetermined region including the eye, a region including the darkest portion and having a brightness equal to or less than a predetermined brightness as the pupil portion, and detects a region including the brightest portion and having a brightness equal to or more than a predetermined brightness as a corneal reflection. The position detector 352 also detects a corneal reflection portion from the captured image and calculates the coordinates indicating the corneal reflection center position. In addition, the position detector 352 calculates each coordinate value of each of the two images captured by the left and right cameras (step S106).

Meanwhile, in order to obtain the three-dimensional world coordinates, the left and right cameras have undergone camera calibration using a stereo calibration method in advance, and thereby the conversion parameter has been calculated. As the stereo calibration method, any conventional method such as the method using the Tsai camera calibration theory is applicable.

The position detector 352 uses this conversion parameter to convert the coordinates of the left and right cameras into the three-dimensional world coordinates of the pupil center and the corneal reflection center (step S107). For example, the position detector 352 defines that the coordinates obtained from the image captured by the left camera 102b with the LED light source 103a lit are the coordinates of the left camera, and that the coordinates obtained from the image captured by the right camera 102a with the LED light source 103b lit are the coordinates of the right camera. These coordinates are converted into the three-dimensional world coordinates by using the conversion parameter. The world coordinate values thus obtained correspond to the world coordinate values to be obtained from the images captured by the left and right cameras when light is assumed to have been emitted from the virtual light source 303. The curvature center calculator 353 calculates the line connecting the world coordinates of the obtained corneal reflection center and the world coordinates of the center position of the virtual light source 303 (step S108). The curvature center calculator 353 next calculates the line connecting the world coordinates of the center of the target image displayed at a point on the screen of the display 101 and the world coordinates of the pupil center (step S109). The curvature center calculator 353 calculates an intersection of the line calculated at step S108 and the line calculated at step S109 and determines this intersection as the corneal curvature center (step S110). The curvature center calculator 353 calculates a distance between the pupil center and the corneal curvature center at this time and stores the distance in the storage 150 or the like (step S111). The stored distance is used later at a time of the gaze point (eye gaze) detection for calculating the corneal curvature center.

In the calculation process, the distance between the pupil center and the corneal curvature center during the gaze at a point on the display 101 is kept constant in a range of detection of the gaze point within the display 101. The distance between the pupil center and the corneal curvature center may be calculated based on an average of all or some of the values that have been calculated during the reproduction of the target image.

Figure 11:
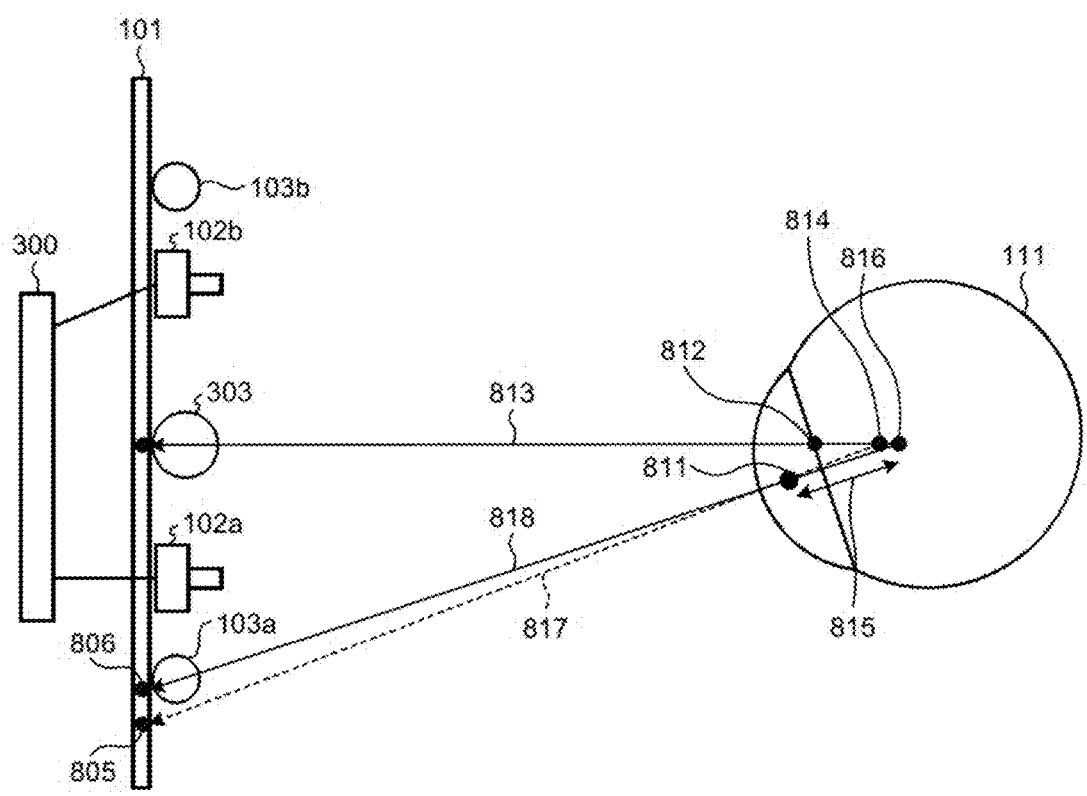
FIG. 11 is a diagram illustrating a method for calculating a corneal curvature center position based on a distance obtained beforehand.

FIG. 11 is a diagram illustrating a method, in the gaze point detection, for calculating a corrected position of the corneal curvature center based on the distance between the pupil center and the corneal curvature center obtained beforehand. A gaze point 805 represents a gaze point obtained from the corneal curvature center calculated based on an ordinary curvature radius value. A gaze point 806 represents a gaze point obtained from the corneal curvature center calculated based on the distance obtained beforehand.

A pupil center 811 and a corneal reflection center 812 correspond to the pupil center position and the corneal reflection center position, respectively, calculated in the gaze point detection. A line 813 is a line connecting the virtual light source 303 and the corneal reflection center 812. A corneal curvature center 814 is a corneal curvature center position calculated from an ordinary curvature radius value. A distance 815 is a distance between the pupil center and the corneal curvature center, which are calculated in the calculation process performed beforehand. A corneal curvature center 816 represents a position of the corneal curvature center calculated using the distance calculated beforehand. The corneal curvature center 816 can be calculated based on the fact that the corneal curvature center exists on the line 813 and the distance between the pupil center and the corneal curvature center is equal to the distance 815. Accordingly, an eye gaze 817 calculated by using an ordinary curvature radius value is corrected into an eye gaze 818. Also, the gaze point on the screen of the display 101 is corrected from the gaze point 805 to the gaze point 806.

Figure 12:
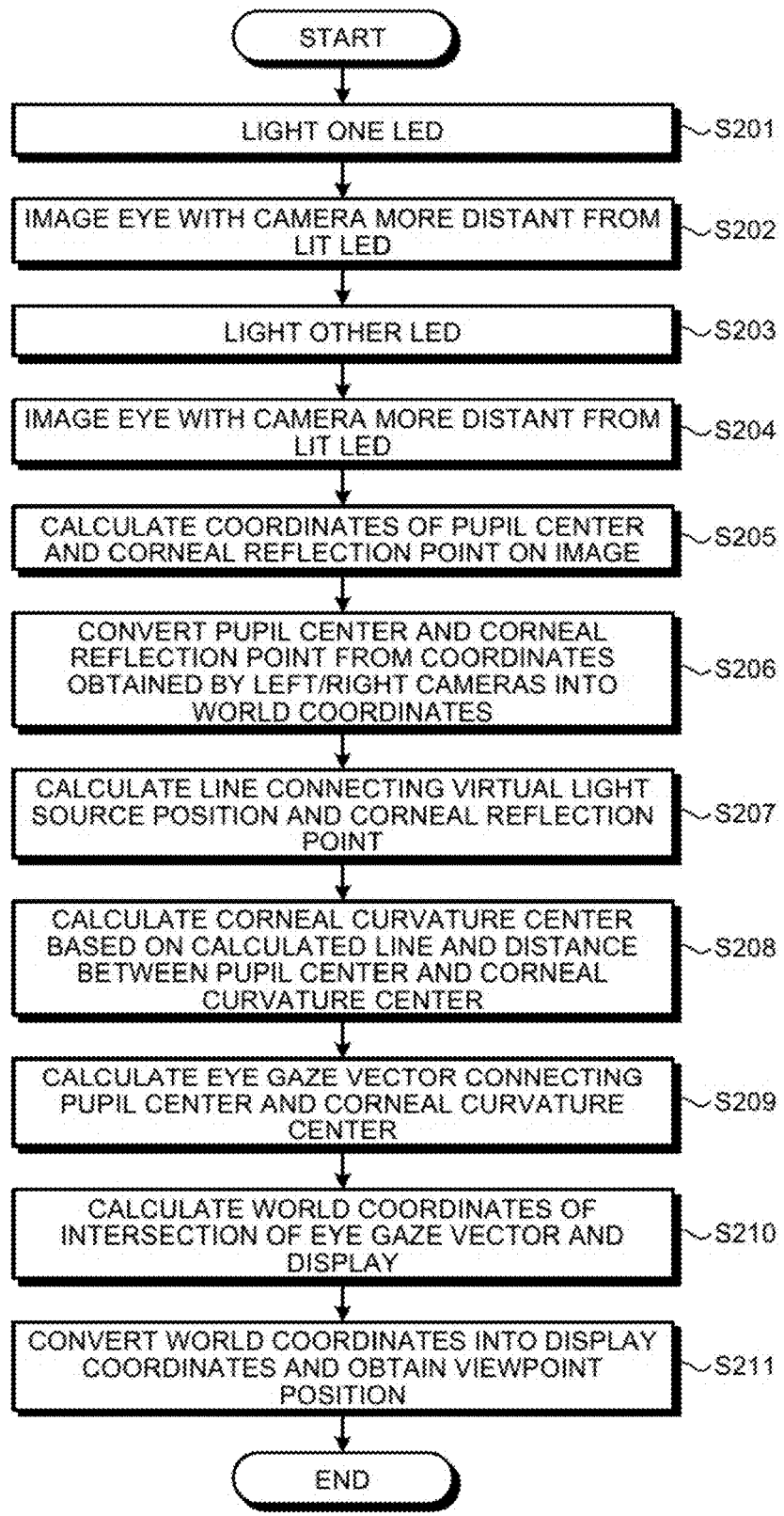
FIG. 12 is a flowchart illustrating an exemplary eye gaze detection process of the present embodiment.

FIG. 12 is a flowchart illustrating an exemplary eye gaze detection process of the present embodiment. For example, the eye gaze detection process in FIG. 12 is executable as a process to detect the eye gaze among diagnostic processes using a diagnostic image. The diagnostic process also includes, other than the steps illustrated in FIG. 12, a process to display the diagnostic image and an evaluation process performed by the evaluator 357 using the detection result of the gaze point.

Steps S201 to S207 are similar to steps S102 to S108 illustrated in FIG. 10 and thus the description thereof will be omitted.

The curvature center calculator 353 calculates, as the corneal curvature center, the position located on the line calculated at step S207 and where the distance from the pupil center is equal to the distance obtained by the calculation process performed beforehand (step S208).

The eye gaze detector 354 calculates a vector (eye gaze vector) connecting the pupil center and the corneal curvature center (step S209). This vector represents the eye gaze direction in which the subject is viewing. The gaze point detector 355 calculates the three-dimensional world coordinates of the intersection between the eye gaze direction and the screen of the display 101 (step S210). This value is the coordinate value, represented by the world coordinate, of the point at which the subject gazes on the display 101. The gaze point detector 355 converts the calculated three-dimensional world coordinate values into the coordinate values (x, y) represented by the two-dimensional coordinate system of the display 101 (step S211). This enables to calculate the gaze point at which the subject gazes on the display 101.

Modification

The calculation process for calculating the distance between the pupil center position and the corneal curvature center position is not limited to the methods described in FIGS. 9 and 10. Hereafter, another exemplary calculation process will be described with reference to FIGS. 13 and 14.

Figure 13:
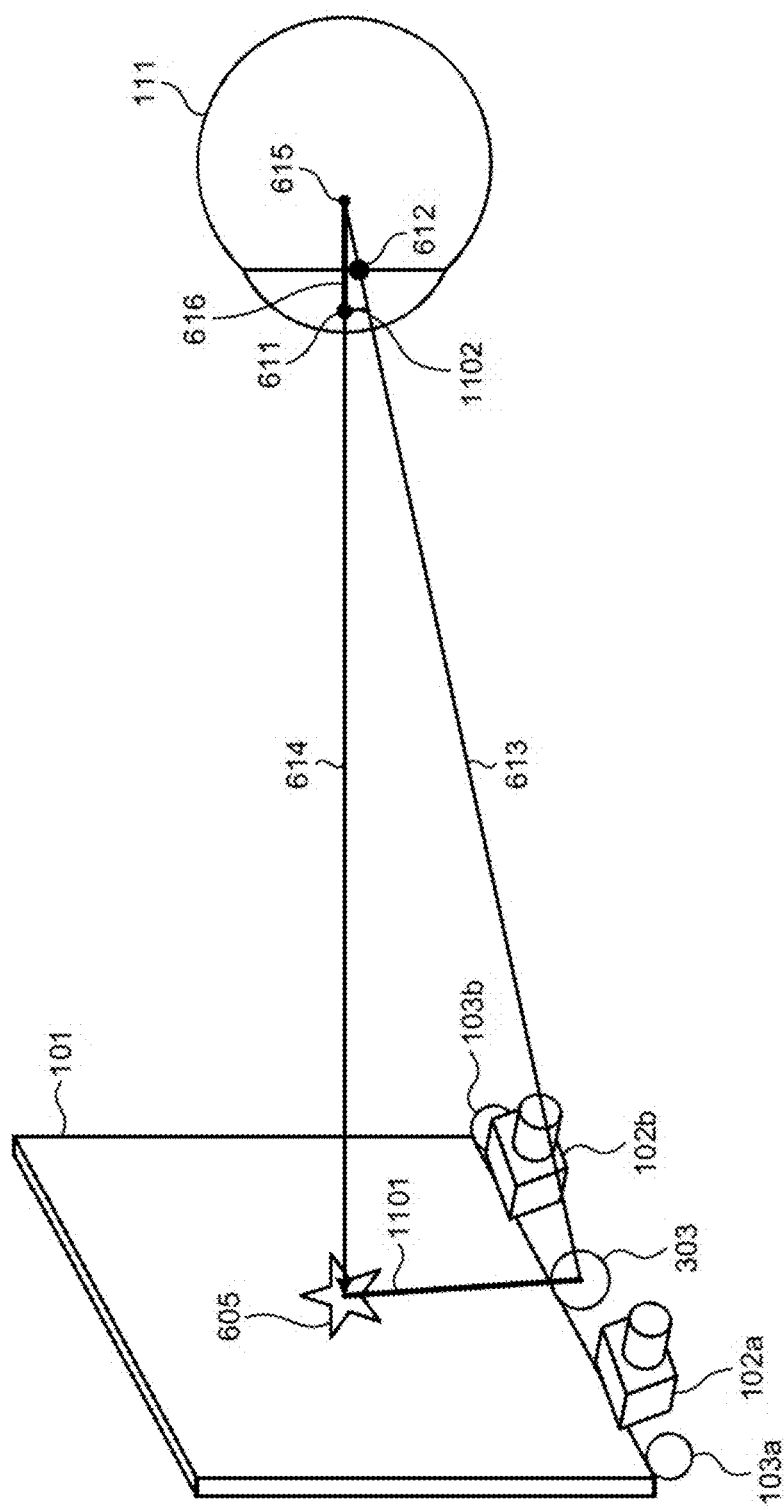
FIG. 13 is a diagram illustrating a calculation process in a modification.

FIG. 13 is a diagram illustrating a calculation process in the present modification. The same reference signs are given to the components described in FIGS. 3 to 6 and 9 and the description thereof will be omitted.

A line segment 1101 is a line segment (first line segment) connecting the target position 605 and the virtual light source position. A line segment 1102 is a line segment (second line segment) that is parallel to the line segment 1101 and connecting the pupil center 611 and the line 613. In the present modification, the distance 616 between the pupil center 611 and the corneal curvature center 615 is calculated using the line segments 1101 and 1102 and stored, as described below.

Figure 14:
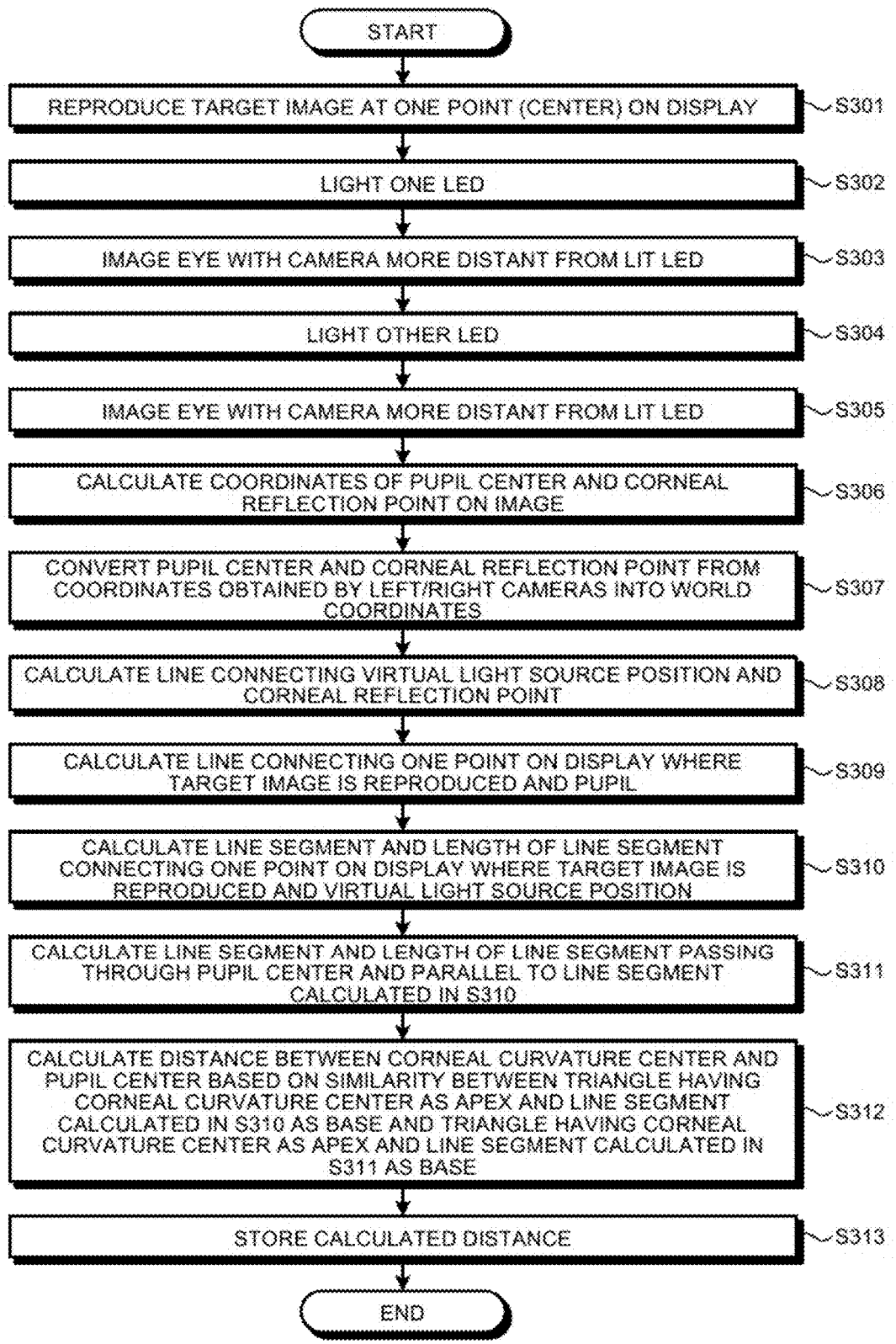
FIG. 14 is a flowchart illustrating an exemplary calculation process in the modification.

FIG. 14 is a flowchart illustrating an exemplary calculation process in the present modification.

Since steps S301 to S309 are similar to steps S101 to S109 illustrated in FIG. 10, the description thereof will be omitted.

The curvature center calculator 353 calculates the line segment (line segment 1101 in FIG. 13) connecting the center of the target image displayed at a point on the screen of the display 101 and the virtual light source position and also calculates the length (L1101) of the calculated line segment (step S310).

The curvature center calculator 353 calculates the line segment (line segment 1102 in FIG. 13) passing through the pupil center 611 and parallel to the line segment calculated at step S310 and also calculates the length (L1102) of the calculated line segment (step S311).

The curvature center calculator 353 calculates the distance 616 between the pupil center 611 and the corneal curvature center 615 based on the similarity between a triangle having the corneal curvature center 615 as a vertex and the line segment calculated at step S310 as a base and a triangle having the corneal curvature center 615 as a vertex and the line segment calculated at step S311 as a base (step S312). For example, the curvature center calculator 353 calculates the distance 616 such that the ratio of the length of the line segment 1102 to the length of the line segment 1101 is equal to the ratio of the distance 616 to the distance between the target position 605 and the corneal curvature center 615.

The distance 616 can be calculated by using the expression (1) as below. Note that L614 is a distance between the target position 605 and the pupil center 611.

$$\text{Distance } 616=(L614 \times L1102)/(L1101-L1102) \quad (1)$$

The curvature center calculator 353 stores the calculated distance 616 in the storage 150 or the like (step S313). The stored distance is used later at a time of the gaze point (eye gaze) detection for calculating the corneal curvature center.

As stated above, the following advantageous effects can be obtained, for example, according to the present embodiment.

(1) Capturing an image by using two cameras and two light sources while lighting one of the two light sources distant from the camera being used makes it possible to capture a darker image of a pupil alone and to improve pupil detection accuracy and eye gaze detection accuracy.

(2) By using one light source distant from the camera being used, the two light sources need not be separated as much as the methods stated in Patent Documents 1 and 2, enabling a compact arrangement.

An eye gaze detection apparatus and an eye gaze detection method according to the present invention can effectively improve detection accuracy.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An eye gaze detection apparatus comprising: a plurality of illuminators each including a light source for emitting light and disposed symmetrically with respect to a virtual light source position; a plurality of imaging units each disposed at an inner or outer position with respect to the plurality of illuminators; an output controller configured to display a target image, at which a subject gazes, at a third position on a display; a position detector implemented by a central processing unit configured to detect a first position indicating a pupil center and a second position indicating a corneal reflection center based on an image of an eyeball of a subject, the image being captured by the imaging unit with the light emitted by the illuminator; and a calculator implemented by the central processing unit configured to calculate a fourth position indicating a corneal curvature center, based on the virtual light source position, the third position, the first position, and the second position, wherein the position detector is configured to detect, from the image of the eyeball of the subject, a region including a brightest portion and having a brightness equal to or more than a predetermined brightness as a corneal reflection, the calculator is configured to calculate a first line connecting the virtual light source position and the second position, and a second line connecting the first position and the third position, and while determining a distance between an intersection of the first and second lines and the first position as a first distance, calculate the fourth position existing on the first line, where a distance from the first position is equal to the first distance, and the calculator is configured to calculate: a first line segment connecting the virtual light source position and the third position; a second line segment that is parallel to the first line segment and starts on the first position and runs toward the first line; and the first distance where a ratio of the second line segment to the first line segment is equal to a ratio of the first distance to a distance between the third position and the fourth position, and the eye gaze detection apparatus detects the eye gaze based on the calculated ratios.

2. The eye gaze detection apparatus according to claim 1, further comprising an illumination controller implemented by the central processing unit configured to control the plurality of illuminators individually such that each illuminator is lit at a different timing, wherein the position detector is configured to detect the first position and the second position based on:

a first image captured by a first imaging unit disposed at a more distant position than any other imaging unit among the plurality of imaging units from a first illuminator when light is emitted by the first illuminator among the plurality of illuminators; and a second image captured by a second imaging unit disposed at a more distant position than any other imaging unit among the plurality of imaging units from a second illuminator when light is emitted by the second illuminator among the plurality of illuminators.

3. The eye gaze detection apparatus according to claim 1, further comprising an eye gaze detector implemented by the central processing unit configured to detect an eye gaze based on the first position and the fourth position.

\* \* \* \* \*